United States Patent [19]

Shimizu et al.

[11] Patent Number: 4,841,949
[45] Date of Patent: Jun. 27, 1989

[54] ENDOSCOPE WITH A DEVICE FOR RAISING A MEDICAL INSTRUMENT

[75] Inventors: Yoshihito Shimizu, Sagamihara; Tatsuya Yamaguchi, Hino, both of Japan

[73] Assignee: Olympus Optical Co., Ltd., Japan

[21] Appl. No.: 130,790

[22] Filed: Dec. 9, 1987

[30] Foreign Application Priority Data

Dec. 10, 1986 [JP] Japan .......................... 61-189110[U]
Jul. 3, 1987 [JP] Japan .......................... 62-101817[U]

[51] Int. Cl.⁴ .............................................. A61B 1/00
[52] U.S. Cl. ...................................................... 128/4
[58] Field of Search ........................................ 128/4, 6

[56] References Cited

U.S. PATENT DOCUMENTS 3,896,793 7/1975 Mitsui et al. ............................ 128/6
4,593,680 6/1986 Kubokawa ............................ 128/4

FOREIGN PATENT DOCUMENTS 3446698 2/1986 Fed. Rep. of Germany .
59-33401 3/1984 Japan .

Primary Examiner—William H. Grieb

[57] ABSTRACT

An endoscope with a device for raising a medical instrument, comprising an operating section and an insertion section having a distal end portion. A storage room having an opening is provided in a distal end portion and a channel duct communicating with the storage room is located in the insertion section. A medical instrument raising block, mounted in the storage room, serves to raise the distal end portion of the medical instrument which, after passing through the channel duct, extends from the opening. A raising operation wire runs through the passageways of the operating section and the insertion section and the distal end of the wire is attached to the medical instrument raising block. A device for preventing the medical instrument from being caught by the wire is formed at the top of one side wall, very close to the wire, of the side walls defining the storage room.

6 Claims, 5 Drawing Sheets

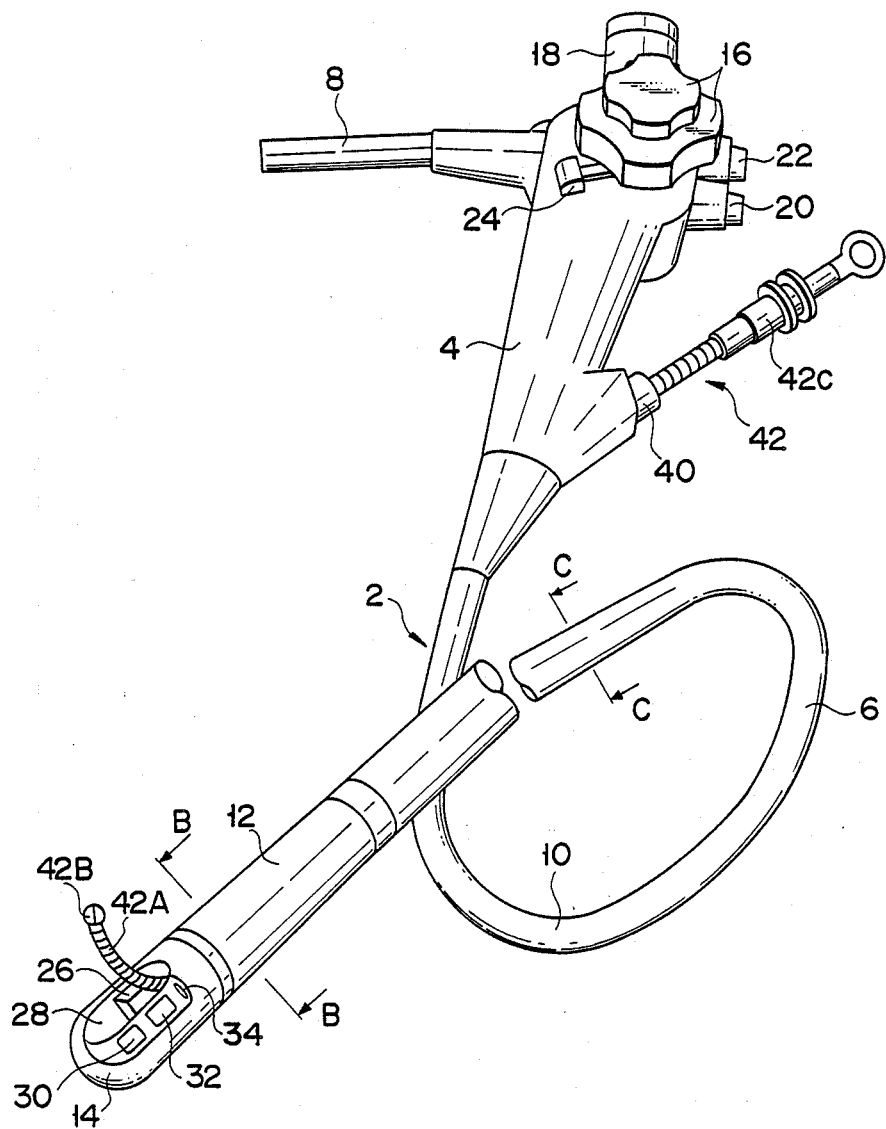
F I G. 1

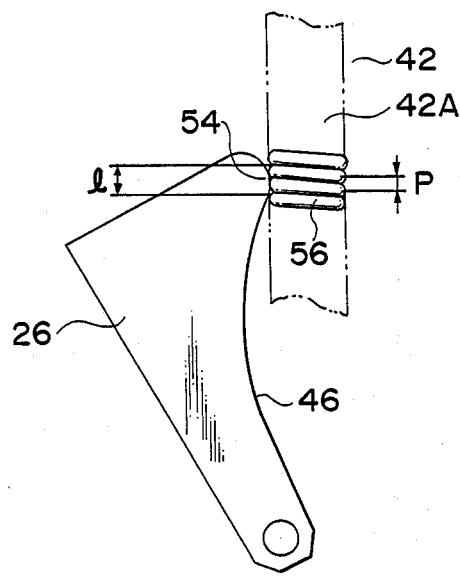
FIG. 3
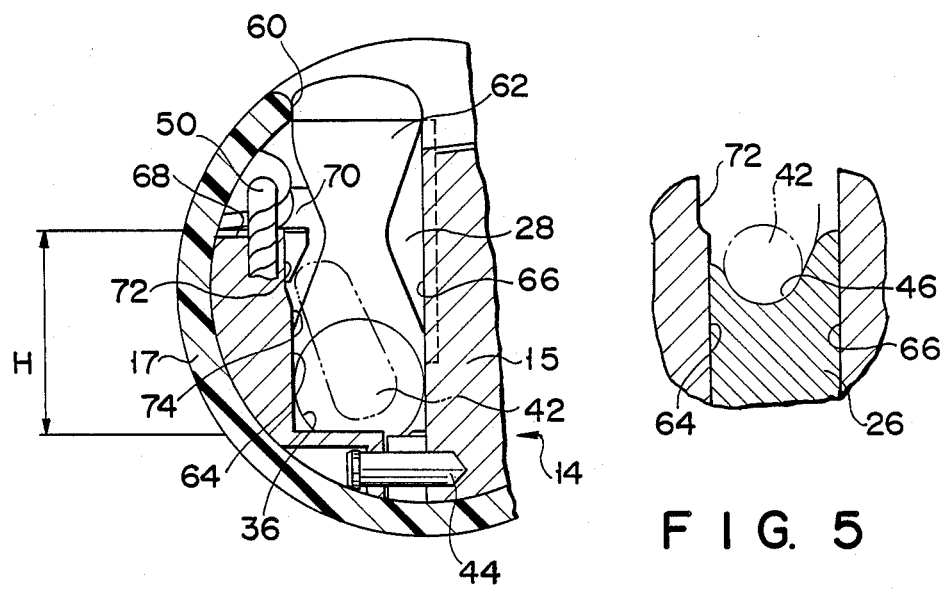
FIG. 4
FIG. 5

ENDOSCOPE WITH A DEVICE FOR RAISING A MEDICAL INSTRUMENT

BACKGROUND OF THE INVENTION

A. Field of the Invention

This invention relates to an endoscope with a channel for inserting a medical instrument and an operating device for raising the distal end portion of the medical instrument which is introduced into the body cavity through the channel.

B. Description of the Prior Art

A typical endoscope has a channel communicating between an operating section and the distal end of an insertion section. Through this channel, a medical instrument such as forceps or a catheter is introduced into the body cavity. A storage room having an opening communicating with the channel is provided in the distal end portion of the insertion section of the endoscope. Stored in this storage room is a raising block for setting a direction in which a medical instrument is introduced into the body cavity.

This raising block is connected to a rotating shaft mounted to the bottom of the storage room. The raising block is connected with a raising operation wire extending from the operating section and is controlled remotely from the operating section. The raising block is stably rotated in a substantially vertical direction as it is guided by the left and right walls of the storage room.

However, in the storage room of the raising block in an ordinary endoscope, one side wall where the raising operation wire is located is relatively low in height. As a result, there is a relatively large space between the top face of the side wall and the raising operation wire. This poses a problem that when a medical instrument is extended into the body cavity through the opening of the storage room, the distal end of the medical instrument enters the space and gets caught by the raising operation wire.

A possible solution to prevent this problem is to raise the height of the side wall very close to the raising operation wire. In this case, however, the resulting increased surface area of the side wall increases the frictional resistance between the side wall face and the raising block, making it difficult to operate the raising block.

In a typical endoscope, as disclosed in Japanese Utility Model Disclosure (Kokai) No. 59-33401, a guide groove for guiding a medical instrument is formed in the top surface of the raising block. Along this guide groove, the distal end of the medical instrument is guided and introduced into the body cavity. The sheath of the medical instrument, however, does not contact the whole length of the guide groove slidingly. The sheath of the medical instrument extended from the storage room into the body cavity slidingly contacts only the distal end edge of the raising block. This means that the medical instrument extended into the body cavity is raised by the distal end edge of the raising block.

As described above, in the conventional raising block, the sheath of a medical instrument which extends from the opening of the storage room is supported by the distal end of the raising block.

The problem with the conventional raising block is that since the sheath of a medical instrument is generally formed of a closely wound coil, when the medical instrument is moved forward and backward while the sheath is supported by the distal end edge of the raising block, the medical instrument sways or moves intermittently each time the coil goes over the edge by one pitch. If the medical instrument moves unstably as mentioned above, it is difficult to bring the distal end of the medical instrument closer to the diseased part in the body cavity. In addition, high-level technique is required and a long time is taken for treatment, increasing the pains of the patient.

When the raising block is turned, the distal end edge of the raising block slides over the sheath of the medical instrument. As a result, the medical instrument vibrates and moves unstably, thus impeding the treatment.

SUMMARY OF THE INVENTION

The object of this invention is to provide an endoscope having a raising operation device capable of extending a medical instrument through the opening of the storage room smoothly and executing a cocking operation of the medical instrument with ease.

The object of this invention can be achieved by the endoscope described in the following. The endoscope comprises an operation section and an insertion section having a distal end portion. The distal end portion is provided with a storage room having an opening. A channel duct communicating with the storage room is located in the insertion section. A medical instrument raising block is arranged in the storage room. This raising block serves to raise the distal end portion of the medical instrument which, after passing through the channel duct, extends from the opening. One end of the raising operation wire is connected with the raising operation knob in the operating section. The other end is fixed to the distal end of the raising block by means of a fixture. A device to prevent the distal end portion of the medical instrument from being caught by the raising operation wire is formed at the top of one side wall, close to the raising operation wire, of the side walls by which the storage room is defined.

The raising block has a flat face to support the medical instrument and to keep smooth contact with the sheath of the medical instrument when the distal end portion of the medical instrument is raised by the raising block.

With the endoscope according to this invention, the frictional resistance between the side wall face of the storage room and the raising block is far lower than in the conventional endoscope and a medical instrument is prevented from being caught by the raising operation wire.

With the endoscope according to this invention, the unstable movements, such as vibration or intermittent movement, of a medical instrument can be prevented when the medical instrument is raised or moved forward and backward.

Therefore, it is possible to extend a medical instrument from the opening smoothly and raise the medical instrument easily.

BRIEF DESCRIPTION OF THE DRAWINGS

FIG. 1 is a perspective view showing an endoscope having a device to raise a medical instrument according to this invention;

FIG. 3 is a side view schematically showing a medical instrument raising block and a sheath of a medical instrument;

FIG. 4 is a sectional view taken along line A—A of FIG. 2;

FIG. 5 is a partial sectional view of the medical instrument raising block;

DETAILED DESCRIPTION OF THE PREFERRED EMBODIMENTS

Figure 2:
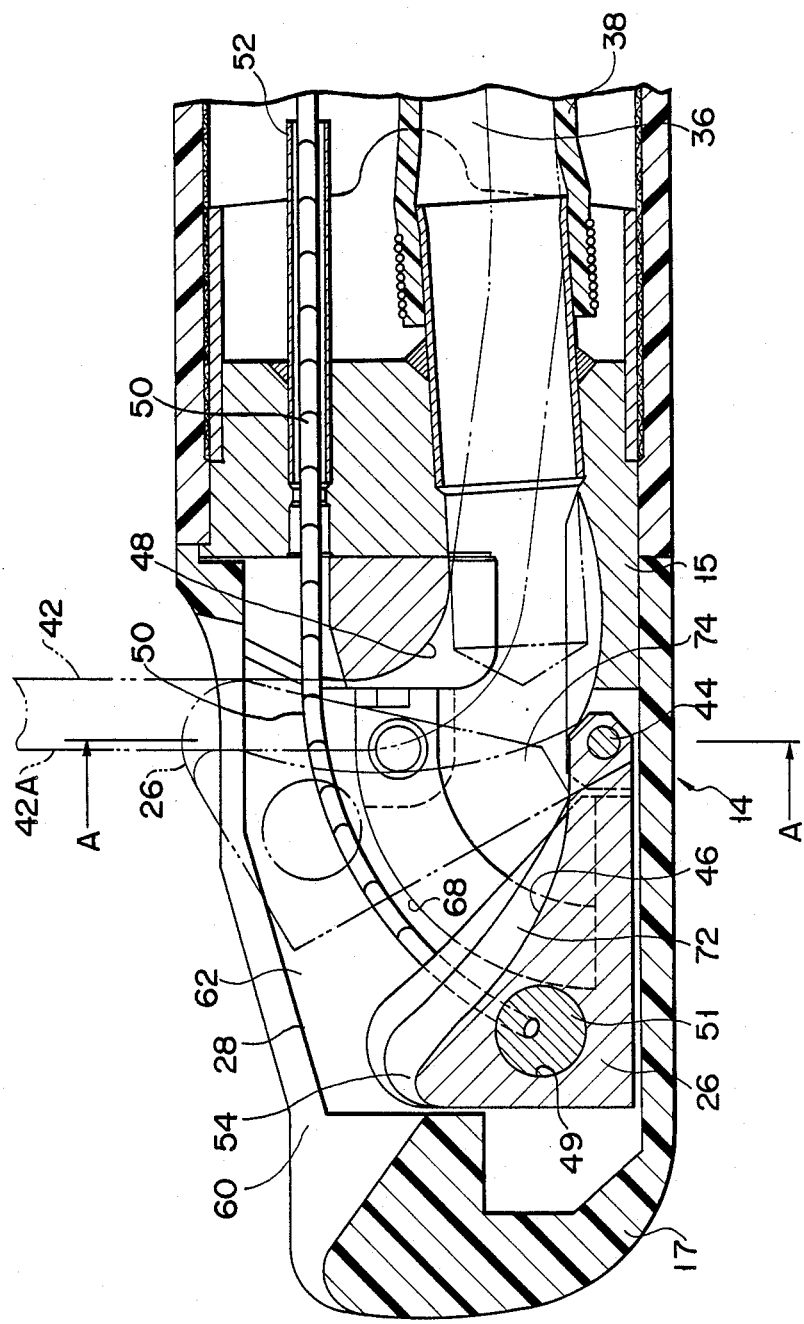
FIG. 2 is a longitudinal sectional view showing the distal end portion of an endoscope according to an embodiment of this invention.

A preferred embodiment of this invention will now be described with reference to the accompanying drawings.

Endoscope 2 of FIG. 1 comprises operating section 4, insertion section 6 and light guide cable 8. The proximal end of flexible portion 10 is connected to operating section 4, the proximal end of bending portion 12 is connected to the distal end of flexible portion 10 and distal end portion 14 is connected to bending portion 12. Bending portion 12 comprises many tubular segments linked in a line. Operating section 4 is provided with angle knob 16. Bending portion 12 is operated remotely by means of a bending operation wire (not shown) which is connected at its one end to angle knob 16 and inserted in insertion section 6. Operating section 4 is provided with eyepiece 18 having an ocular, air/water supply control button 20, suction control button 22 and raising operation knob 24 to remotely operate medical instrument raising block 26.

In the endoscope according to this embodiment of the invention, the substantial bending length of bending portion 12, e.g., the distance from the linkage point of the forefront and adjacent tubular segments to the linkage point of the hindmost and adjacent tubular segments is set at a value in a range from 38 mm to 42 mm, while the length of the hard portion in distal end portion 14, that is to say, the length from the linkage point of the forefront and adjacent tubular segments to the distal end of distal end portion 14 is set at a value in a range from 27 mm to 31 mm. By giving dimensions as mentioned above to the bending portion and distal end member, it is possible to make cannulation easy with an endoscope of a side-view type.

Storage room 28 to accommodate medical instrument raising block 26 has an opening in the periphery of distal end portion 14. Storage room 28 is provided along its side with objective cover glass (observation port) 30, light guide cover glass (lighting port) 32 and air/water supply nozzle 34. Storage room 28 communicates with medical instrument channel 36. Medical instrument channel 36 is formed by tube 38 located inside insertion section 6 and communicates with medical instrument inserting hole 40 formed at the underside of operating section 4. Through this medical instrument inserting hole 40, channel 36 and storage room 28, medical instrument 42 such as forceps can be introduced into the body cavity.

Referring to FIG. 2, raising block 26 located in storage room 28 is at its proximal end attached rotatably to shaft 44 mounted at the bottom of storage room 28. Groove 46 for guiding medical instrument 42 is formed on the top surface of raising block 26. On the inner wall of storage room 28 which faces guide groove 46 of raising block 26, there is formed circular support 48 to guide sheath 42A of medical instrument 42 which is raised.

The distal end portion of raising block 26 which has mounting hole 49 is connected to the distal end of raising operation wire 50 by means of fixture 51. The proximal end portion of raising operation wire 50 is passed through wire guide 52 located in insertion section 6 and connected to raising operation knob 24 at operating section 4. By operating raising operation knob 24, operation wire 50 is moved accordingly and thereby raising block 26 can be operated remotely.

As shown in FIG. 1, medical instrument 42 has sheath 42A. Sheath 42A is provided at its distal end with treating element 42B and at its proximal end with operating handle 42C. Sheath 42A of medical instrument 42 is formed of a pipe having a closely wound spring.

Support portion 54 of raising block 26 for supporting sheath 42A when medical instrument 42 is introduced into the body cavity is provided with a flat face having a specified length as shown in FIG. 3. If the winding pitch of wire 56 of sheath 42A is defined by P, the length l of support portion 54 is $P \leq l$. The length l of support portion, or flat face 54 is set such that wire 56 of sheath 42A contacts flat face 54 continuously when medical instrument 42 is moved.

Next, the operation of the medical instrument and the endoscope will now be described. Medical instrument 42 is introduced into the body cavity through medical instrument inserting hole 40 of operation section 4, passing instrument channel 36 and storage room 28. Treating element 42B at the distal end of medical instrument 42 is guided along guide groove 46 of raising block 26 in storage room 28. To raise medical instrument 42 which is led out from the opening of storage room 28, raising operation knob 24 of operating section 4 is operated to pull raising operation wire 50. As a result, as indicated by the two-dot chain line in FIG. 2, raising block 26 is turned, flat face 54 pushes up sheath 42A of medical instrument 42 and sheath 42A is pressed against circular support 48. Thus, sheath 42A of medical instrument 42 is raised along circular support 48. To be more specific, sheath 42A of medical instrument 42 is raised and its lead-out direction is set, both according to the amount of rotation of raising block 26. The ranges of angle at which medical instrument 42 is raised are set for different models of the endoscope.

In the raising operation, flat face 54 raises sheath 42A of medical instrument 42 while scraping thereon as raising block 26 rotates. This means that flat face 54 of raising block 26 keeps a sliding contact with sheath 42A of medical instrument 42. The sliding contact length l of flat face 54 is larger than the winding pitch P of wire 56 of spring 42A. In the embodiment of FIG. 3, since the sliding contact length l is twice the pitch P $(l=2P)$, the flat face of support portion 54 continuously and smoothly contacts any of the peaks of wire 56 constituting sheath 42A. Neither intermittent contact nor heavy movement occurs. Even when medical instrument 42 is moved forward and backward, the peaks of wire 56 constituting sheath 42A keeps smooth contact with flat face 54. Hence, medical instrument 42 moves stably, free from vibration and intermittent movement.

The construction of the distal end portion of the endoscope of this invention will now be described in greater detail. Distal end portion 14 of FIG. 6 has housing 15 coated with resin cover 17, opening 60 is formed at the top face of cover 17 and flat face portion 58 of housing 15 is exposed from opening 60. Flat face portion 58 of housing 15 has observation port 30 and lighting port 32 provided in the axial direction of the insertion section. Adjacent observation port 30 and lighting port 32, there is elongated storage room 28 formed along the axial direction of the insertion section. As shown in FIG. 4, the whole storage room 28 is tilted in the direction of observation port 30 and lighting port 32. Opening 62 of storage room 28 is located close to observation port 30 and lighting port 32.

Raising block 26 is accommodated in storage room 28. Left-side wall 64 and right-side wall 66 of storage room 28 are located close to the side faces of raising block 26, respectively, as shown in FIGS. 4 and 5. Left-side wall 64 near raising operation wire 50 has a relatively higher height H. Top face 68 of left-side wall 64 has a circular form to minimize space 70 right below raising operation wire 50, excepting the part where raising operation wire 50 passes. Recessed part 72, which is not flush with the side wall of raising block 26, is formed at the peripheral area of left-side wall where raising operation wire 50 passes. Recessed part 72 is in a circular-arc form with a constant width, located with the axis of rotation of raising block as the center of curvature, as shown in FIG. 2. The side wall positioned more inside than recessed part 72 forms sliding contact face 74 contacting the side face of raising block 26.

Figure 6:
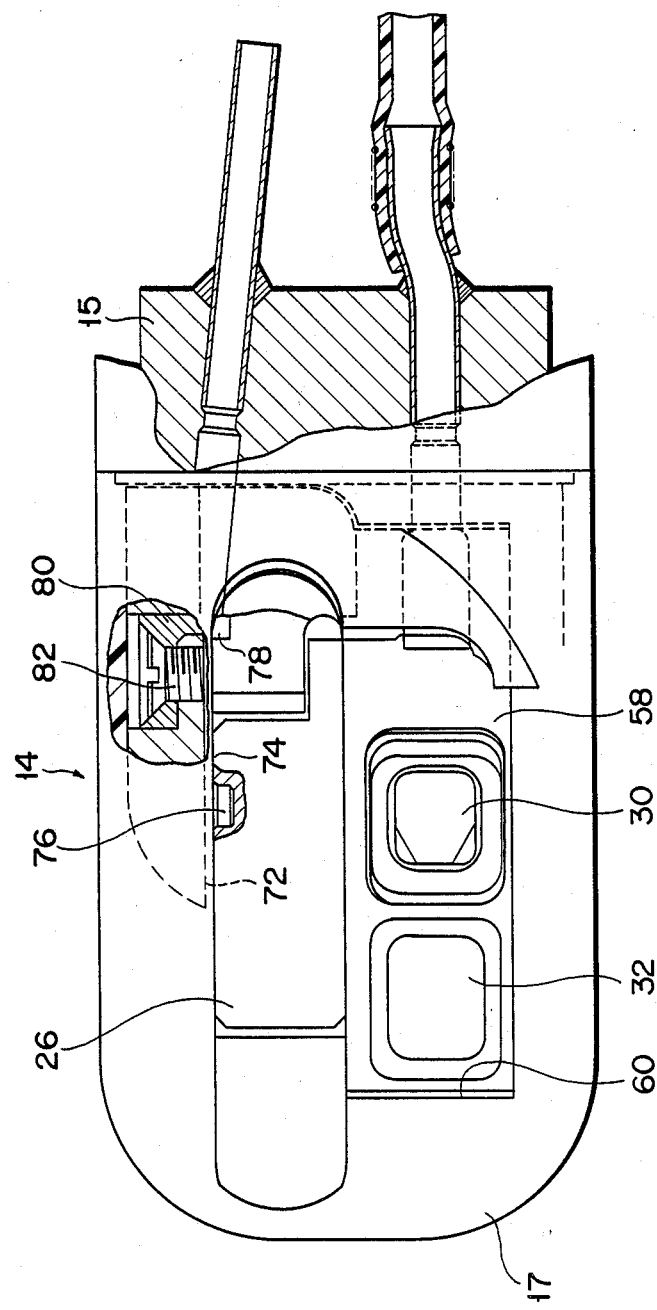
FIG. 6 is a plan view, partly in cross section, of the distal end portion of the endoscope of FIG. 2.

As shown in FIG. 6, TEFLON chip 76 is fitted in the side face of raising block 26 in such a manner as to lightly slide on sliding contact face 74 of left-side wall 64. By use of this chip 76, frictional resistance between raising block 26 and side wall 64 is reduced. Stopper 80 projecting into storage room 28 is secured at a rear position of left-side wall 64 by means of set screw 82. This stopper limits the maximum rising angle for raising block 26.

Figure 7:
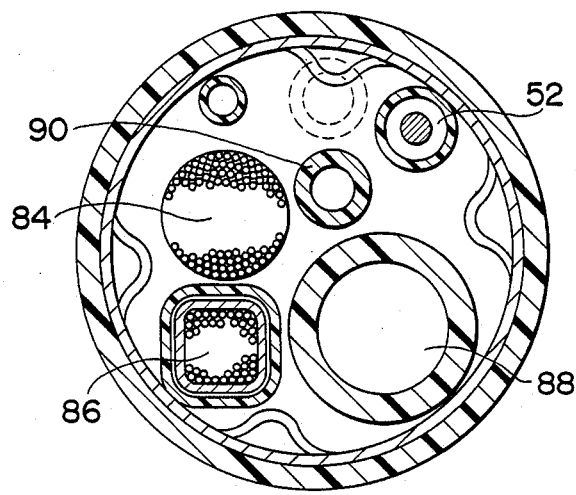
FIG. 7 is a sectional view taken along line B—B of FIG. 1.
Figure 8:
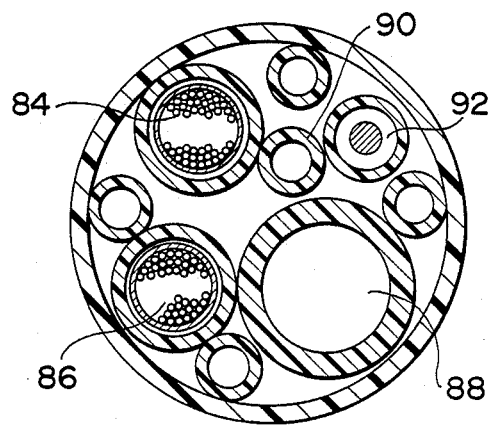
FIG. 8 is a sectional view taken along line C—C of FIG. 1.

FIG. 7 shows a sectional view of insertion section 6 in the vicinity of distal end portion 14. In this part, wire guide tube 52, image guide fiber 84, light guide fiber 86, forceps channel 88 and air/water supply tube 90 are arranged dispersedly in the internal space of insertion section 6. At the middle part of insertion section 6, wire guide 92 connected to wire guide tube 52 and air/water tube 90 are arranged concentratedly in the center as shown in FIG. 8. Also arranged near the center of the insertion section is focus wire guide (not shown) to adjust the focal length of the objective optical system (not shown) disposed at the distal end. By the arrangement of those members near the center of the insertion section, it is possible to correctly raise forceps and perform a focusing operation when the insertion section is bent.

As set forth above, in the endoscope according to this invention, left-side wall 64 where raising operation wire 50 is passed is given a relatively greater length with the result that space 70 right below raising operation wire 50 can be minimized. Therefore, it is possible to prevent a trouble that the distal end of medical instrument 42, which is guided and raised by raising block 26, enters space 70 and is caught therein. Recessed part 72 which does not come into sliding contact with raising block 26 is formed at a part of side wall 64 located closely to the side face of raising block 26. Hence, the frictional resistance between side wall 64 and raising block 26 can be reduced substantially, making it easy to operate the raising block.

What is claimed is:

1. An endoscope having a device for raising a medical instrument, comprising:
    an operating section;
    an insertion section having a distal end portion in which a storage room having an opening is provided;
    a channel duct located in said insertion section and communicating with said storage room;
    a medical instrument raising block arranged in said storage room, said medical instrument raising block being used to raise the distal end portion of a medical instrument which, after passing through said channel duct, extends from said opening;
    a raising operation wire running through internal passageways of said operating section and said insertion section, the distal end of said operation wire being attached to said medical instrument raising block; and
    means for preventing the medical instrument from being caught by said operation wire, said means being formed at the top of one side wall, closest to said operation wire, of the side walls defining said storage room.

2. The endoscope according to claim 1, wherein said means consists of a side wall having a circular top face very close to said operation wire.

3. The endoscope according to claim 2, wherein said means consists of a recessed part in a circular arc formed at the peripheral area of said side wall.

4. The endoscope according to claim 1, wherein said medical instrument raising block has support means to support the medical instrument and contact a sheath of the medical instrument smoothly when the distal end portion of the medical instrument is raised.

5. The endoscope according to claim 4, wherein said medical instrument has a sheath consisting of a closely wound spring, and said support means has a flat face with a length of more than one pitch of said spring.

6. An endoscope having a device for raising a medical instrument, comprising:
    an operating section;
    an insertion section having a distal end portion in which a storage room having an opening is provided;
    a channel duct located in said insertion section and communicating with said storage room;
    a medical instrument raising block arranged in said storage room, said medical instrument raising block being used to raise the distal end portion of a medical instrument which, after passing through said channel duct, extends from said opening;
    a raising operation wire running through internal passageways of said operation section and said insertion section, the distal end of said operation wire being attached to said medical instrument raising block; and
    support means formed at the upper end edge of said medical instrument raising block and used to support and contact a sheath of the medical instrument smoothly when the distal end portion of the medical instrument is raised, said sheath consisting of a closely wound spring and said support means having a flat face with a length of more than one pitch of said spring.

* * * * *